US005849523A

United States Patent [19]

Afanasiev et al.

[11] Patent Number: 5,849,523

[45] Date of Patent: Dec. 15, 1998

[54] *AEDES AEGYPTI* DENSOVIRUS EXPRESSION SYSTEM

[75] Inventors: Boris N. Afanasiev; Jonathan Ored Carlson; Barry J. Beaty, all of Fort Collins, Colo.; David R. Higgins; Kelly J. Thibault, both of San Diego, Calif.

[73] Assignee: Research Corporation Technologies, Inc., Tucson, Ariz.

[21] Appl. No.: 485,341

[22] Filed: Jun. 7, 1995

Related U.S. Application Data

[63] Continuation-in-part of Ser. No. 334,669, Nov. 4, 1994, Pat. No. 5,627,048.

[51] Int. Cl.[6] .............................. C12P 21/06; C12N 5/06; C12N 15/86

[52] U.S. Cl. ....................... 435/69.1; 435/320.1; 435/348

[58] Field of Search ........................ 536/24.1; 435/320.1, 435/69.1, 348, 975

[56] References Cited

PUBLICATIONS

Afanasiev et al. (1991) "Nucleotide sequence and genomic organization of Aedes Densonucleosis virus" *Virology* 185:323–336.

Giraud et al. (1992) "The densovirus of *Junonia–coenia* (JcDNV) as an insect cell expression vector" *Virology* 186:207–218.

Igarashi et al. (1978) "Isolation of a Singh's *Aedes albopictus* cell clone sensitive to Dengue and Chikungunya viruses" *J. Gen. Virol.* 40:531–544.

Lebedinets et al. (1978) "A study of the effect of the densonucleosis virus of the mosquito *Aedes aegypti* L. of the preadult stages of differen species of blood sucking mosquitoes" *Mikrobiologicheskli Zhurnal* 40:352–356.

Afanasiev et al. (Nov. 17, 1994) "Densovirus of *Aedes aegypti* as an expression vector in mosquito cells" *Experimental Parasitology* 79:322–339.

Boublik et al. (1994) "Complete nucleotide sequence and genomic organization of the *Aedes albopictus* parvovirus (AaPV) pathogenic for *Aedes aegypti* larvae" *Virology* 200(2):752–763.

*Primary Examiner*—George C. Elliott
*Assistant Examiner*—Terry A. McKelvey
*Attorney, Agent, or Firm*—Scully, Scott, Murphy & Presser

[57] ABSTRACT

The present invention is directed to use of *Aedes aegypti* densonucleosis virus (Aedes DNV or AeDNV) as a heterologous gene expression system. The invention described herein provides promoters from the *Aedes aegypti* genome such as the p.05, p7 and p61 promoters to generate expression vectors with cloning sites for insertion of heterologous genes. The invention further provides expression vectors comprising an AeDNV promoter operably linked to a heterologous gene and insect host cells comprising the vectors of the invention. Methods of producing recombinant proteins utilizing the vectors of the invention are also provided. The present invention further provides a kit containing the vectors of the invention for production of a recombinant protein.

12 Claims, 11 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Lys Arg Lys Arg
1
```

( 2 ) INFORMATION FOR SEQ ID NO:2:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Met Lys Phe Leu Val Asp Val Ala Leu Val Phe Met Val Val Tyr Ile
1               5                   10                  15

Ser Tyr Ile Tyr Ala
            20
```

*AEDES AEGYPTI* DENSOVIRUS EXPRESSION SYSTEM

CROSS REFERENCE TO RELATED APPLICATION

This application is a continuation-in-part of U.S. application Ser. No. 08/334,669 filed Nov. 4, 1994, U.S. Pat. No. 5,627,048.

The invention described herein was made in the course of and under grant number N1H-5 R01 AI25629-05 from the National Institute of Health and is therefore subject to the rights of the U.S. government.

FIELD OF THE INVENTION

The present invention relates to an expression system useful for introducing genetic material into host cells. In particular, it relates to use of the *Aedes aegypti* densonucleosis virus (AeDNV) genome in infectious, non-lytic expression vectors for insect host cells. The present invention provides three AeDNV promoters useful for control of expression in host cells: the p0.5 promoter, the p61 promoter and the p7 promoter. In addition, specific portions of the AeDNV genome provide targeting sequences for localized expression within a host cell.

BACKGROUND OF THE INVENTION

The *Aedes aegypti* densonucleosis virus (Aedes DNV or AeDNV) is a member of the heterogenous group of densoviruses (family Parvoviridae) that infect invertebrates (mostly insects) (Siegl et al., 1985*, Intervirology*, 23:61–73; Tijssen, P., 1990*, Handbook of Parvoviruses*, P. Tijssen, Ed., CRC Press, Boca Raton, Fla.).

Parvoviridae are small (18–28 nm) icosahedral nonenveloped viruses containing single-stranded linear DNA genomes of 4 to 6 kb in length. A typical parvoviral genome consists of a long coding region flaked by terminal hairpin structures of 115 to 365 nucleotides (nt) at each end. The coding region of a parvovirus genome is occupied almost entirely by two long consecutive open reading frames (ORFs). The left ORF codes for a major nonstructural protein (NS1) containing a sequence with a nucleotide binding motif and the right ORF encodes the capsid proteins (VPs) (Cotmore and Tattersal 1987*, Advances in Virus Research* 33:91–174). Smaller ORFs encoding additional non-structural proteins are also found in the genome of most parvoviruses. Usually, only one strand ("plus") of the genome of mammalian parvoviruses is used to code for virus proteins (Cotmore and Tattersal 1987). The densovirus infecting *Junonia coenia* however, has coding sequences for its structural proteins located on the "minus" strand (Giraud et al. 1992*, Virology* 186:207–218; Dumas et. al., 1992*, Virology* 191:202–222).

AeDNV was originally isolated from a laboratory colony of *A. aegypti* (Lebedeva et al., 1973*, Acta Virologica* 17:253–256). The virus is infectious to mosquito larvae of the genera Aedes, Culex, and Culiseta when introduced into the water in which they are reared. Anopheles larvae can be infected only by injection. The virus can infect all stages of larvae, pupae, and the adults of both sexes. Almost all tissues of larvae show cytopathological evidence of infection including fat body, muscles, hindgut, imaginal disks, malpighian tubules, ovaries, and others (Buchatsky, L. P., 1989*, Diseases of Aquatic Organisms* 6:145–150). The virus particles are typical of a parvovirus, with a diameter of 18–20 nm. They are resistant to organic solvents such as chloroform, to pH between 4 and 11, and to prolonged incubation at 50° C. (Buchatsky 1989).

The sequence of the cloned AeDNV viral genome shows many characteristics typical of a parvovirus genome (Afanasiev et al. 1991*, Virology* 185:323–336). The virion DNA is about 4000 nt in length with palindromic sequences capable of forming Y-like secondary structures at each end. The palindromic sequences contain cis-acting signals required for DNA replication and encapsidation (Diffoot et al., 1989*, J. Virol.* 63:3180–3184). The leftward position of the AeDNV genome is occupied by a large ORF (left ORF) that encodes the AeDNV NS1 protein of about 97.5 kDa. The right ORF of the AeDNV genome could encode a capsid protein (VP) of about 40 kDa, which is in good agreement with the sizes of proteins observed from purified virus (approximately 40 and 38 kDa). Presumably the smaller protein is derived from the larger by proteolytic cleavage of a small peptide fragment from the amino terminus, as occurs in many of the mammalian parvoviruses. Besides having the smallest genome and the shortest VPs among known parvoviruses, AeDNV is also unique in the following features: a second ORF (mid ORF) capable of encoding a protein of 41 kDa is located completely within the left ORF and there is also an ORF in the negative strand capable of encoding a protein of 26 kDa. Little is known, however, about the virus gene expression, including whether all of the ORFs observed in the AeDNV genome are transcribed and translated into proteins (Afanasiev, 1991).

Another mosquito densovirus (AaPV) has been isolated recently from *Aedes albopictus* C6/36 cell line (Jousset et al. 1993*, Virus Research* 29:99–114). The analysis of the AaPV genome showed that this virus is closely related to AeDNV (Boublik et al. 1994*, Virology* 200:752–763). These viruses share 77.3% nucleotide and between 73 and 78% amino acid sequence homologies. The organization of the AaPV genome is also similar to that of AeDNV except that no potential ORF has been found on the minus strand of AaPV (Boublik et al. 1994).

In recent years several types of viruses have been successfully used as vectors for introduction and expression of foreign genes in eukaryotic cells. Parvoviruses exhibit several features that are beneficial for developing such expression vectors (Carter, B. J., 1990*, Handbook of Parvoviruses*, P. Tijssen, Ed., CRC Press, Boca Raton, Fla., pp. 247–284). The genome of parvoviruses are among the smallest of animal DNA viruses known and hence, easier to handle for cloning and transfection procedures. It has been shown that a cloned parvovirus genome transfected into eukaryotic cells can be rescued from the plasmid vector and replicate as a wild-type virus (Samulski et al. 1982*, Proc. Natl. Acad. Sci. USA* 79:2077–2081). The promoter for the parvovirus capsid gene is very efficient for expression of foreign genes, especially when trans-activated (Rhode, S. L., 1985*, Journal of Virology* 55:886–889).

Parvovirus vectors have been used to introduce and express different foreign genes in mammalian cells. (Tratschin et al., 1984*, Molecular and Cellular Biology* 5:3251–3260; Hermonat and Muzyczka 1984*, Proc. Natl. Acad. Sci. USA* 81:6466–6470; Carter 1990; Muzyczka, N., 1992*, Current Topics in Microbiology and Immunology* 158:97–129; Russel et al., 1992*, Journal of Virology* 66: 2821–2828). Recombinant parvovirus genomes carrying a foreign gene can be encapsidated into infectious particles if complemented in trans with capsid and the nonstructural (NS1 and NS2) proteins. Because the genome of a human parvovirus, adeno-associated virus (AAV), is able to integrate into cell chromosomes, special attention was given to develop a stable expression vector from this virus (Cheung et al., 1980, *Journal of Virology* 33:739–748; Hermonat and Muzyczka 1984, *Proc. Natl. Acad. Sci. USA* 51:6466–6470. Tratschin et al. 1985, *Molecular and Cellular Biology* 5:3251–3260; Lebkowski et al. 1988, *Molecular and Cellular Biology* 8:3988–3996).

Densoviruses present an attractive opportunity to develop expression vectors for insects. Unfortunately, this group has been studied much less than mammalian parvoviruses. The cloned *Junonia coenia* densovirus (JcDNV) has been used to express β-gal when fused into the one open reading frame (ORF1) located on the plus DNA strand and transfected into insect SPC-SL 52 cells. However, because there is only one ORF on the plus strand of the JcDNV genome, the number of heterologous genes which can be inserted into a JcDNV expression vector is limited.

In addition, virions produced in the JcDNV expression system are poorly infectious in SPC-SL 52 transfected cells. The poor infectivity prevents cell to cell spreading of the virus and results in a rapid drop of virus titer after few passages. (Giraud et al., 1992).

*Galleria mellonella* densovirus (GmDNV), closely related to JcDNV has been exploited recently as an expression vector injected into larvae of its natural host, *Galleria mellonella* (greater wax moth). However, a major impediment to the study of GmDNV gene expression is the absence of a tissue culture host for the virus. Ta1 and Attathom 1993, *Archives of Insect Biochemistry and Physiology* 22:345–356).

Baculovirus has also been used as an expression system in insect cells. A drawback of the Baculovirus expression system is that the Baculovirus lyse their insect host cells causing reductions in yield and other complications in isolating and purifying recombinantly expressed protein. Lysis of the Baculovirus host cells also prevents its use in the generation of DNA libraries. A further drawback of the baculovirus system is that direct cloning is not possible in this system.

Thus, there is a need for a densoviral expression system for use in host cells which is highly infectious and non-lytic. Also desired is a densoviral expression system which can express several different heterologous genes in one vector. Integration of the densoviral genome and heterologous coding sequence into the host cell genome is also desired so that stably expressing cell lines can be generated. Finally, host cell/expression vector combinations in which the densovirus virions are highly infectious without being cytopathic are needed.

SUMMARY OF THE INVENTION

The present invention is directed to use of *Aedes aegypti* densonucleosis virus (Aedes DNV or AeDNV) as a heterologous gene expression system. The invention described herein provides promoters from the *Aedes aegypti* genome such as the p0.5, p7 and p61 promoters to generate expression vectors with cloning sites for insertion of heterologous genes. The invention further provides expression vectors comprising an AeDNV promoter operably linked to a heterologous gene and insect host cells comprising the vectors of the invention. Methods of producing recombinant proteins utilizing the vectors of the invention are also provided. The present invention further provides a kit containing the vectors of the invention for production of a recombinant protein.

DETAILED DESCRIPTION OF THE INVENTION

Figure 1:
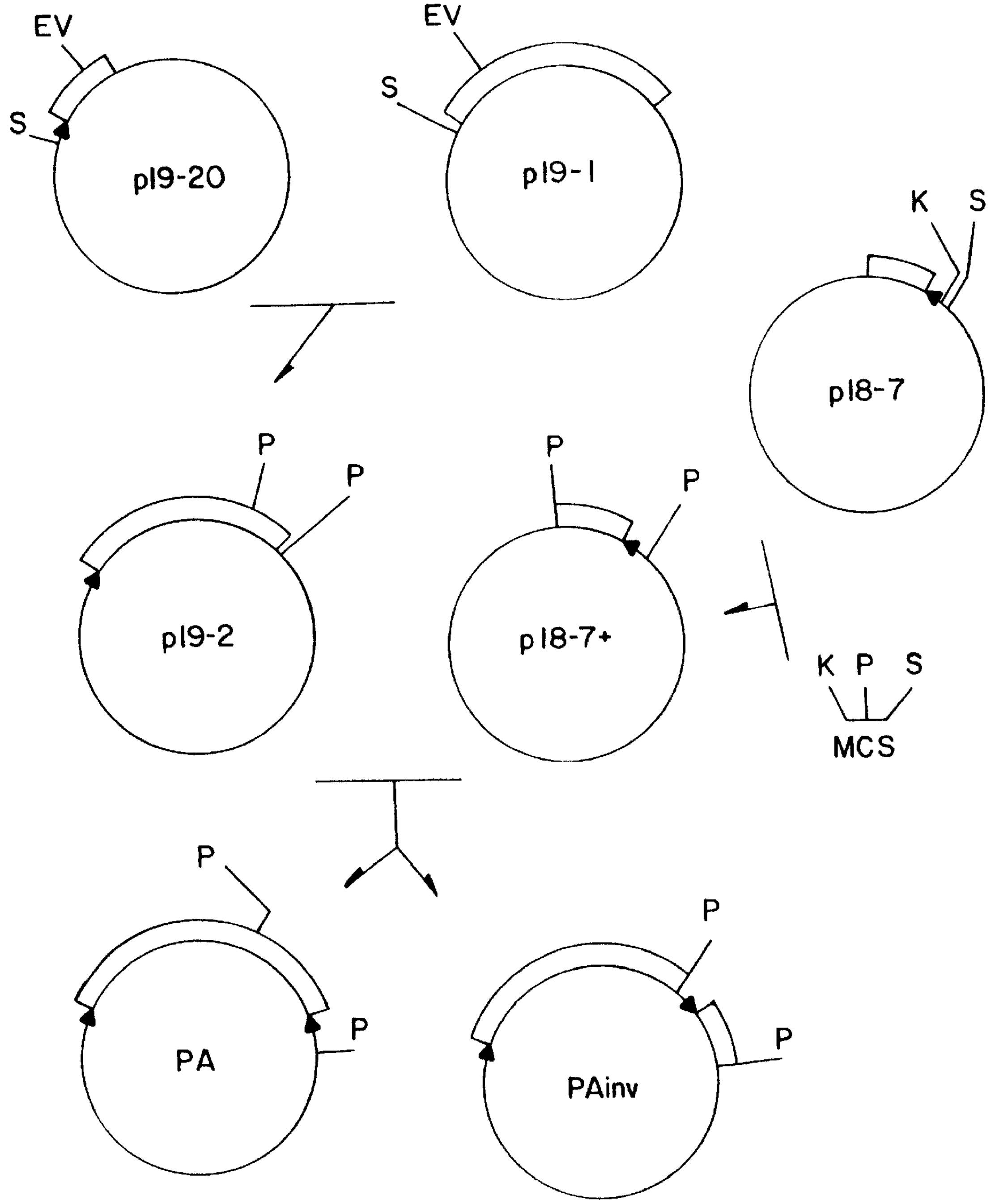
FIG. 1 depicts the scheme used to construct pUCA and pUCAinv. Black triangles represent the terminal structures of the AeDNV genome. MCS refers to the fragment containing multiple cloning sites purified from "pBLUESCRPT" KS phagemid.

The present invention relates to a densovirus expression system useful for the expression of heterologous proteins in permissive host cells. More particularly, the present invention is directed to densoviral expression vectors of *Aedes aegypti* which can be transfected into permissive host cells.

In accordance with the present invention, it has been surprisingly found that *Aedes albopictus* C6/36 cells are permissive for the *Aedes aegypti* densoviral (AeDNV) vectors described herein. C6/36 cells infected with the AeDNV vectors of the present invention show no cytopathic effects even though AeDNV has been shown to be highly pathogenic to mosquito larvae (see, e.q., Buchatsky, 1989, *Diseases of Aquatic Organisms* 6:145–150.

The present invention provides AeDNV promoters which can be used for efficient expression of foreign genes in mosquito cells. In accordance with the present invention, three promoters have been identified and are shown to be capable of driving expression of a heterologous gene. The p7 and p61 promoters which drive expression of the putative AeDNV NS2 (nonstructural protein) and VPs (capsid proteins), respectively, yield similar high levels of expression. A third promoter, p0.5, is also provided which exhibits low levels of expression detected only when stimulated in trans with the AeDNV nonstructural proteins. All three promoters are located on the plus strand of the AeDNV genome.

In accordance with the present invention, the promoters of AeDNV have been shown to be useful in the production of heterologous recombinant proteins. Accordingly, the present invention provides an isolated DNA consisting essentially of the p0.5 promoter of AeDNV, an isolated DNA consisting essentially of the p7 promoter of AeDNV, and an isolated DNA consisting essentially of the p61 promoter of AeDNV.

The promoters of the present invention may also be used with varying amounts of the coding sequence for the AeDNV protein expressed by the promoter. In particular, the present invention also provides an isolated fragment of the AeDNV genome consisting essentially of the p0.5 promoter and the coding region of about the first 47 amino acids of NS1; an isolated fragment of the AeDNV genome consisting essentially of the p7 promoter and the coding region of about the first 22 amino acids of NS2; and an isolated fragment of the AeDNV genome consisting essentially of the p61 promoter and the coding region of about the first 38 amino acids of VP; and an isolated fragment of the AeDNV genome consisting essentially of the p61 promoter and the coding region of the VPs (VP1 and VP2).

The AeDNV promoter and the isolated fragments of AeDNV containing promoters and coding regions are useful in the construction of vectors for the expression of heterologous proteins. Heterologous in this context refers to any protein that is not encoded natively by the AeDNV genome.

The vectors of the present invention comprise the 5' and 3' termini of AeDNV required for excision from the vector and replication as a wild-type virus. The terminal sequences are known in the art and described by Afanasiev et al. (1991) *Virology* 185:323. The entire terminal sequences are not required as long as sufficient nucleotides are present to maintain a terminal hairpin structure. The ordinarily skilled artisan can determine the sufficient nucleotides to maintain the hairpin structure necessary for excision and replication. In a preferred embodiment, 35 nucleotides can be deleted from the 5' terminus defined by Afanasiev et al. (1991) with maintenance of the hairpin structure.

In the vectors of the present invention, the AeDNV termini flank at least one expression cassette. As used herein, "expression cassette" refers to a nucleotide sequence capable of expressing a particular gene if said gene is inserted so as to be operably linked to the regulatory regions present in said nucleotide sequence. The expression cassette may comprise an AeDNV promoter operably linked to the coding sequence of a heterologous gene. In another embodiment the AeDNV promoter is adjacent to a cloning site, for example a multiple cloning site, such that upon insertion of the coding region of a heterologous gene into the cloning site, the promoter is operably linked to the coding sequence. Operably linked in this context means that the promoter and the coding sequence are positioned such that the promoter effectuates transcription of the coding sequence.

More than one expression cassette may be present within the AeDNV termini. Accordingly, more than one heterologous gene may be expressed by one vector. Further, it is within the ken of the ordinarily skilled artisan to include other sequences such as selectable markers, signal sequences, and the like.

Use of the p61 promoter and the coding sequence for the first 38 amino acids from the N-terminus of the putative AeDNV VP1 in an expression vector provides localized expression predominantly in the nuclear area of the host cells. Located within the 38 amino acid sequence is the sequence: KRKR (SEQ ID NO:1) which is highly basic in character and similar to nuclear localization sequences in other viruses. Thus, the present invention provides sequences useful for targeting heterologous proteins to the nucleus.

Use of the p7 promoter and the coding sequence for the first 22 amino acids from the N-terminus of the putative AeDNV NS2 in expression vectors provides localized expression predominantly in the cytoplasm of host cells. Thus the present invention also provides sequences useful for targeting heterologous protein material to specific locations within the host cell.

Use of the p61 promoter and the coding sequence of AeDNV VP1 and VP2 in an expression rector provides the expression of AeDNV structural proteins in a host cell. Cells transformed by such a vector provide a packaging system for recombinant protein production.

The vectors of the present invention can be constructed by standard techniques known to one of ordinary skill in the art and found, for example, in Sambrook et al. (1989) in *Molecular Cloning: A Laboratory Manual*, or any of a myriad of laboratory manuals on recombinant DNA technology that are widely available. A variety of strategies are available for ligating fragments of DNA, the choice of which depends on the nature of the termini of the DNA fragments and can be readily determined by the skilled artisan. The sequence of the AeDNV genome may be found in Afanasiev et al. (1991).

The AeDNV expression vectors of the present invention may also contain other sequence elements to facilitate vector propagation, isolation and subcloning; for example, selectable marker genes and origins of replication that allow for propagation and selection in bacteria and host cells. Examples of selectable marker genes for use in the AeDNV expression vectors particularly suited for insect cells include Zeocin, G418 and hygromycin phosphotransferase. The present invention also contemplates the use of signal peptides for secretion or nuclear localization. Examples include the honey bee melittin excretion peptide comprising the sequence

M K F L V D V A L V F M V V Y I S Y I Y A (SEQ ID NO:2)

and the AeDNV nuclear localization signal KRKR (SEQ ID NO:1). Coding sequences of heterologous genes, sequences for selectable markers, signal sequences and multiple cloning sites are also known to the ordinarily skilled artisan.

In order to demonstrate the ability of the AeDNV promoters of the present invention to control the production of protein products as discovered in accordance with the present invention, novel DNA constructs were constructed. The *E. coli* lacZ gene was placed in several plasmids under the control of the p0.5, p7 and p61 AeDNV promoters. Those of skill in the art recognize that the scope of the present invention is not limited to the production of β-galactosidase under the control of the AeDNV promoters described herein. There are a myriad of peptides and polypeptides which can be produced under the regulation of the promoters disclosed by the present invention. Examples of proteins which can be produced by the AeDNV expression system of the present invention include cytochromes, cytokines, lymphokines (interferons, interleukins), growth factors, therapeutic proteins, vaccines, Hepatitis B surface antigen or any other useful protein desired to be produced. The heterologous gene may also code for a selectable marker such as neomycin resistance in eukaryotes. Selectable markers such as adenine phosphoribosyl transferase (APRT) in APRT deficient cells, ZEOCIN or hygromycin resistance are contemplated. Many well known procedures exist for the preparation of DNA sequences which code for the desired peptide or polypeptide. For example, oligonucleotides of various lengths can be synthesized by known procedures. Several such oligonucleotides can be assembled into longer, double stranded molecules. Alternatively, DNA molecules having the desired coding sequences can be synthesized by use of the enzyme reverse transcriptase using messenger RNA related to the desired polypeptide as a template for the action of reverse transcriptase (cDNA cloning). Another possibility for preparing DNA sequences for expression behind AeDNV promoters is the cloning of genomic DNA fragments obtained from a gene bank or library. In many instances, the DNA encoding the protein of interest is commercially available.

The DNA sequence which codes for the desired peptide or polypeptide can be modified for preparation of the promoter-structural gene construct by a variety of procedures. For example, the ends of the DNA prepared as described above can be ligated with the enzyme DNA ligase to short double-stranded DNA molecules which contain the nucleotide sequence recognized by specific restriction endonucleases, so called linker molecules. Digestion of these molecules with a specific restriction endonuclease following the ligation will generate termini corresponding to the specified restriction endonuclease recognition site at the ends of the prepared DNA sequence.

Figure 3A:
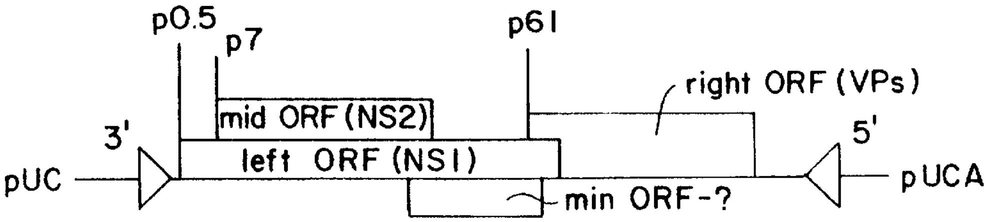
FIGS. 3(*a*)–3(*f*) depicts the organization of the AeDNV genome and structure of recombinant expression plasmids PUCA, pUCAP0.5, pUCAP7, PUCAP61, pUCAPmin and PUCANS2. Open reading frames (ORFs) for nonstructural proteins (NS1 and NS2), structural proteins (VPs) and ORF detected in the minus strand (min ORF) are represented by open bars and promoters for these ORFs by p0.5, p7 and p61. Terminal structures of the AeDNV genome are indicated as 3' (left) and 5' (right) black triangles. The lacZ gene is not drawn to scale.

Three specific AeDNV promoter-β-galactosidase gene constructs prepared in the course of developing the present invention are described in terms of the genome organization data presented in FIG. 3*a*. Based upon the consensus eukaryotic promoter sequences and location of the large ORF in the AeDNV genome, putative promoters were identified at map units 0.5, 7 and 61 (taking the length of the AeDNV genome as 100 map units), just upstream of the left ORF, the mid ORF and the right ORF, respectively.

Genome organization of AeDNV is depicted in FIG. 3*a* and is derived from Afanasiev et al., 1991*, Virology* 185:323–326. The leftward position of the AeDNV genome is occupied by a large ORF (left ORF) that encodes the AeDNV NS1 protein. The right ORF of the AeDNV genome encodes the capsid proteins VP1 and VP2. The mid ORF encodes the NS2 protein and is located completely within the left ORF. There is also an ORF (min ORF) in the minus strand capable of encoding a protein of 26 kDa.

The AeDNV promoter-β-galactosidase gene constructs are depicted in FIGS. 3(*b*) through (*e*). In pUCAP0.5, the lacz given is inserted into the left ORF (NS1) and contains 47 amino acids of the putative AeDNV NS1 (FIG. 3*b*).

Figure 3B:
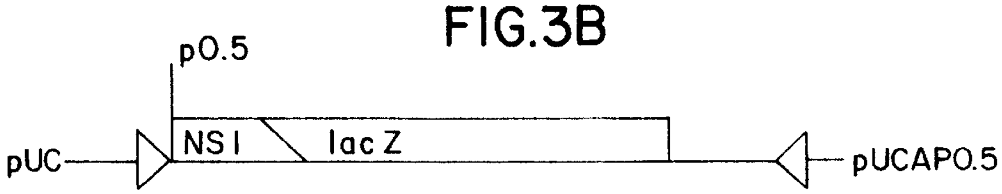
Figure 3C:
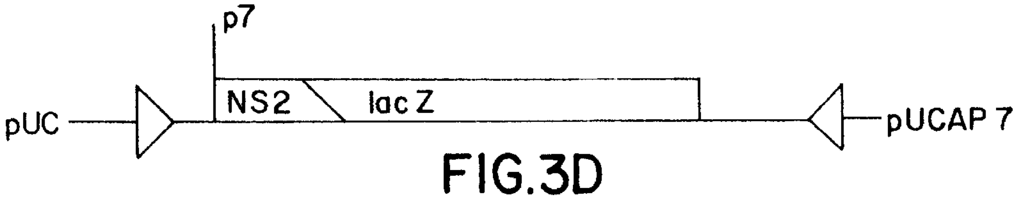

In pUCAP7, the lacZ gene is inserted into the mid ORF and contains 22 amino acids from the N-terminus of the putative AeDNV NS2. (FIG. 3*c*).

Figure 3D:
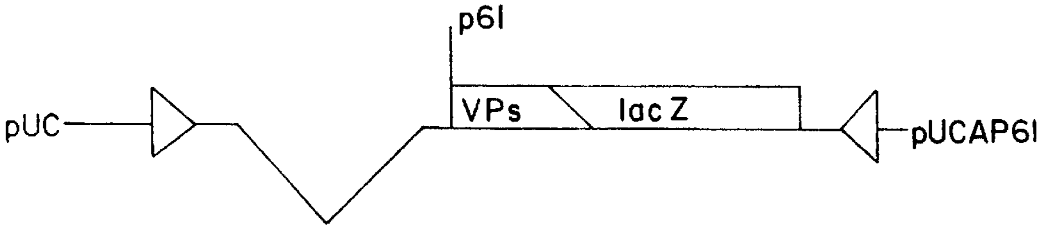

In pUCAP61, the lacZ gene is inserted into the right ORF and contains 38 amino acids from the N-terminus of the putative AeDNV VP1. (FIG. 3*d*).

In addition to containing the AeDNV promoter-β-galactosidase gene fusion described above and depicted in FIGS. 3(*b*) through (*e*) the exemplified expression plasmids contain pUC sequences, including the origin of replication, $Amp^R$ gene and terminal sequences of the AeDNV genome which support secondary structures.

The original AeDNV genomic clone used in the development of the present invention did not contain the entire AeDNV genome. Approximately 31 nucleotides from the right (5') end of the genome and, possibly some nucleotides from the left (3') extremity were lacking. However, both ends preserve enough nucleotides to support the secondary structures (hairpins) which are necessary for the excision of the AeDNV genome from a bacterial plasmid and for replication in the host cell.

The expression vectors of the present invention have the ability to transfect a host cell, and the AeDNV-heterologous gene portion is able to excise from the plasmid and replicate in the host cell.

Although the introduction into host cells of the AeDNV constructs of the present invention is exemplified herein employing plasmids as the vehicle for introduction, those of skill in the art recognize that it is not necessary for the construct to be introduced into a host cell via a plasmid. Hence, any molecule capable of being maintained in permissive host cells can be employed. Therefore, the promoter-structural gene constructs of the invention can be manipulated via vectors other than plasmids.

The present invention provides host cells comprising the vectors of the present invention. The host cells are obtained by methods known to one of ordinary skill in the art, for example by transduction or transfection. Transfection may be accomplished by known methods, for example liposome mediated transfection, calcium phosphate mediated transfection, microinjection and electroporation. A host cell is defined herein as any cell into which the AeDNV expression vector of the present invention can be introduced by standard methods of transfection and transduction. In a preferred embodiment, the host cell is an insect cell. *Spodoptera frugiperda* cells including Sf9 are particularly contemplated.

In another preferred embodiment the insect cell is a mosquito cell. Mosquito cells of the genera Aedes, Culex and Culiseta are preferred.

Insect cell lines *A. albopictus* C6/36 (ATCC Accession No. CRL-1660), *A. albopictus* (ATCC Accession No. CCL-126) and *A. aegypti* (ATCC Accession No. CCL-125) can be used in the practice of the present invention. Especially preferred is the *A. albopictus* cell line C6/36. In addition, *Aedes albopictus* INV 126B was deposited with the American Type Culture Collection, 12301 Parklawn Drive, Rockville, Md., 20852, on Jul. 23, 1996 and has been accorded ATCC Accession No. CRL-12158. *Aedes aegypti* cell line C6/36, INV 1660B, was also deposited on Jul. 23, 1996 and assigned ATCC Accession Number CRL-12157. *Aedes aegypti* INV 125B has also been deposited with the ATCC on the same date and accorded ATCC Accession No. CRL-12159.

Host cells that constitutively express the AeDNV structural genes VP1 and VP2 are preferred as host cells. Such host cells can be provided by transfecting a host cell with a vector that expresses VP1 and VP2, preferably under the control of the p61 promoter. Host cells expressing VP1 and VP2 can be transfected by vectors capable of expressing a desired peptide or protein to provide transucing particles, which can then be used to infect permissive cells in order to produce large amounts of the desired peptide or protein. In a preferred embodiment, the present invention provides *A. albopictus* C6/36 cells than consututively express VP1 and VP2. In another preferred embodiment, C6/36 cells are transformed by a vector comprising the coding regions of VP1 and VP2 under the control of the p61 promoter.

The host cells used in the present invention can be grown by attached growth or suspension culture. *Aedes albopictus* clone C6/36 (Igarashi, 1978, *Jour. Gen. Virol.* 40:531–544) can be purchased from the American Type Culture Collection (ATCC Accession No. CRL-1660). Cells are grown at 28° C. in Leibovitz's L-15 medium (Gibco) supplemented with 10% fetal bovine serum (Biowhittaker). Falcon tissue culture flasks for attached growth can be purchased from VWR Scientific. When cell monolayers reach confluence, cells are detached by trypin/versene (Biowhittaker) and passaged 1:4 to 1:10. The medium is changed upon passage or every three to four days. 100 ml suspension culture flasks (spinner) can be purchased from Bellco Glass. Cells are passaged 1:10 upon confluence (>$10^6$ cells/ml) and kept in suspension by stirring at approximately 60 rpm. Unlike other eukaryotic cell lines C6/36 cells adapt well to suspension cell culture.

Cell stocks can be preserved as follows:

1 ml aliquots ($5\times10^6$ cells/ml) of C6/36 cells, resuspended in fresh growth medium supplemented with 10% DMSO, are transferred to cryotubes (Corning). The cryotubes can be placed into styrofoam racks and placed at −20° C. for 2 hours, then transferred to −80° C. for overnight incubation. Frozen cultures can be then be transferred to liquid nitrogen for permanent storage.

C6/36 host cell transfection can be performed by liposome mediated transfection, electroporation or calcium phosphate mediated transfection. Liposome mediated transfections can be performed according to the method detailed in Invitrogen Corporation's "MAXBAC" manual version 1.6, substituting medium, plasmids and cells, where appropriate. Both methods utilize "INSECTIN", insect cell-specific liposomes (Invitrogen Corporation). Electroporation can be performed with 20 $\mu$g of each plasmid DNA, $4\times10^6$ cells in 500 $\mu$l cold 1× PBS (Biowhittaker), using an Electroporator II (Invitrogen Corporation) set at 250 volts, 1000 $\mu$F, and infinite ω. Calcium phosphate mediated transfection is well known in the art and can be performed using Invitrogen Corporation's calcium phosphate transfection kit and protocol.

It has been surprisingly discovered in accordance with the present invention that p7 promoter trans-activation by AeDNV NS1 and NS2 results in a 4–7 fold increase in expression of heterologous proteins by the vectors of the invention. Accordingly, in a preferred embodiment of the invention, the AeDNV NS1 and NS2 genes are used to trans-activate the p0.5, p7 or p61 promoters contained within the heterologous gene expression vectors.

Trans-activation of the promoters of the present invention can be achieved in a number of different ways. Cotransfecting cells with a helper vector comprising the p0.5 promoter and the left ORF (containing within itself p7 and the mid ORF) is one method and means. Accordingly, the present invention further provides an expression vector comprising the AeDNV p0.5 promoter and the left ORF. Such an expression vector is capable of expressing NS1 and NS2. Alternatively, the NS1 and NS2 coding regions can be present under the control of a strong promoter capable of driving NS1 and NS2 expression in insect cells. Thus in such a two vector AeDNV expression system, one plasmid encodes the NS1 and NS2 while a second plasmid comprises at least one of the p61, p7 or p0.5 promoter and coding sequence for a desired peptide or polypeptide.

Alternatively, cells can be transfected with a one vector system comprising the 5' and 3'-termini of AeDNV flanking at least one expression cassette comprising one of the AeDNV promoters operably linked to the coding sequence of a desired peptide or polypeptide and a second expression cassette comprising the p0.5 promoter and the left ORF (containing within itself the mid ORF). In either of these two embodiments, the AeDNV 5' and 3'-terminal repeats necessary for excision of the AeDNV DNA sequence from the plasmid are preferably present at the 5' and 3' extremities of the AeDNV insert in the helper vector.

In yet another aspect of the invention, a one vector system is employed where a host cell line that stably expresses NS1 and NS2 is transfected with an AeDNV expression vector comprising the 5' and 3'-termini of AeDNV flanking at least one expression cassette comprising the AeDNV promoter operably linked to coding sequence of at least one desired protein. NS1 and NS2 genes are expressed by the host cells either chromosomally or extra-chromosomally.

In another aspect of the invention, transducing particles are produced by the following method and means: a first host cell line is cotransfected with a first vector comprising the 5' and 3'-terminal repeats of AeDNV flanking at least one expression cassette comprising an AeDNV promoter operably linked to the coding region of at least one desired peptide or polypeptide and a second helper vector comprising the full length AeDNV genome or sufficient amount of the genome to complement that provided by the first vector. The infectious virions are obtained from the cotransfected host cells and used to transduce a second noninfected host cell line. The second host cell line is cultured under conditions whereby the desired peptide or polypeptide is expressed. The recombinant protein material is then recovered.

In a further aspect of the invention, a host cell line that stably expresses VP1 and VP2 is transfected with an AeDNV expression vector comprising the 5' and 3' terminal repreats of AeDNV flanking at least one expression cassette comprising an AeDNV promoter operably linked to the coding region of at least one desired peptide or polypeptide. Further, NS1 and NS2 genes are expressed by the host cells either chromosomally or extrachromasomally, for example by co-transfecting host cells with an expression vector comprising the coding regions of NS1 and NS2 under the control of a promoter capable of driving NS1 and NS2 expression in insect cells. Infectious virions are obtained from the transfected host cells and used to infect a second noninfected host cell line. The second host cell line is then cultured under conditions whereby the desired peptide or polypeptide is expressed. The recombinant protein material is then recovered.

The foregoing identification of AeDNV promoters, construction of novel vectors, and methods of transfection and transduction provide novel methods of producing a recombinant protein. In one embodiment, the present invention provides a method of producing a recombinant protein comprising: transfecting an insect cell with an expression vector comprising the 5' and 3'-termini of AeDNV, wherein said termini flank at least one expression cassette comprising an AeDNV promoter operably linked to the coding sequence for said recombinant protein, culturing said cell under conditions whereby said protein is expressed; and recovering said protein. Depending upon the nature of the recombinant protein (e.g. secreted, cytoplasmic, nuclear, etc.) the skilled artisan can determine appropriate methods for recovery of the recombinant protein. The ordinarily skilled artisan can similarly determine appropriate cell culture conditions for expression.

As discovered in accordance with the present invention, expression of heterologous proteins from AeDNV promoters can be activated, or increased, by the AeDNV nonstructural proteins. The nonstructural proteins can be provided by co-transfection with a vector capable of expressing NS1 and NS2, or by including the NS1 and NS2 coding regions in the vector expressing the heterologous protein, or by providing cell lines that stably express NS1 and NS2 for transfection by the vector expressing the heterologous gene.

Accordingly, the present invention further provides a method of producing a recombinant protein comprising: co-transfecting an insect cell with a first expression vector comprising the 5' and 3'-termini of AeDNV flanking at least one expression cassette comprising an AeDNV promoter operably linked to the coding sequence for a heterologous protein, and a second expression vector comprising a fragment of AeDNV comprising the p0.5 promoter and the left open reading frame, culturing said cell under conditions whereby said protein, NS1 and NS2 are expressed, and recovering said protein. In another embodiment, the second expression vector comprises the coding regions of NS1 and NS2 operably linked to at least one promoter capable of promoting expression in an insect cell.

In another embodiment, the present invention provides a method of producing a recombinant protein comprising: transfecting an insect cell with an expression vector comprising the 5' and 3'-termini of AeDNV flanking at least one expression cassette comprising an AeDNV promoter operably linked to the coding sequence for a heterologous promoter, and an expression cassette comprising the p0.5 promoter and the left ORF of AeDNV; culturing said cell under conditions whereby said protein, NS1 and NS2 are expressed, and recovering said protein.

In yet another embodiment, the present invention provides a method of producing a recombinant protein comprising: transfecting an insect cell that stably expresses NS1 and NS2 with an expression vector comprising the 5' and 3'-termini of AeDNV flanking at least one expression cassette comprising an AeDNV promoter operably linked to the coding sequence of said protein; culturing said cell under conditions whereby said protein is expressed, and recovering said protein.

In each of the foregoing methods, transfection can be accomplished by methods known to one of ordinary skill in the art, including, for example, liposome mediated transfection, calcium phosphate mediated transfection and electroporation.

A recombinant protein can also be produced in accordance with the present invention by transduction. In particular, the present invention provides a method of producing a recombinant protein comprising: co-transfecting a first insect cell with a first vector comprising the 5' and 3'-termini repeats of AeDNV flanking at least one expression cassette comprising an AeDNV promoter operably linked to the coding region of said protein and a second vector capable of expressing any of AeDNV NS1, NS2 and VP not expressed by said first vector; obtaining infectious virions from said co-transfected cells; infecting a second insect cell with said infectious virions; culturing said second cell under conditions whereby said protein is expressed; and recovering said recombinant protein from said second insect cell.

The present invention provides a further method of producing a recombinant protein comprising: transfecting a first insect cell with a first vector capable of expressing VP1 and VP2 to provide host cells stably expressing VP1 and VP2; cotransfecting said host cells with a second vector comprising an AeDNV promoter operably linked to the coding region of said protein and a third vector capable of expressing NS1 and NS2; obtaining infectious virions from said co-transfected cells; infecting a second insect cell line with said infectious virions; culturing said cells under conditions whereby said protein is expressed; and recovering said recombinant protein from said second insect cell.

Since the p61, p7 and p0.5 promoters are located on the plus strand of the AeDNV genome, multiple expression in one vector can be achieved by providing multiple expression cassettes. In addition, since the promoters express at different levels with p61 being the strongest, p7 being less strong and p0.5 being the weakest, stoichiometric amounts of gene product can be produced. Thus where a specific polypeptide composed of different subunits is desired to be produced recombinantly in an AeDNV expression vector, an AeDNV promoter can be chosen having a strength matched to the amount of a particular subunit needed for proper assembly of the polypeptide. For example, to mimic the levels of Hepatitis B surface antigen synthesized during a typical Hepatitis B infection, and to allow the assembly of subviral particles, the pre-S2/S gene can be placed under control of the p61 promoter while the pre-S1 gene can be placed under control of the p7 or p0.5 promoter.

In that promoters for nonstructural genes are generally early promoters and VP promoters are late promoters, the identification of the p0.5, p7 and p61 promoters also allows the use of the present method to temporally regulate protein expression. For example, two or more proteins can be expressed at different times from the same vector by placing heterologous genes under the control of different AeDNV promoters.

The AeDNV expression vectors of the present invention are also useful in constructing expression libraries since AeDNV recombinants can be accomplished in vitro as the genome of AeDNV is plasmid-borne. Such direct cloning is not possible with other insect viral expression systems e.g. Baculovirus. The recombinant genomes can then be used for transient expression in insect cells and, if complemented in trans with capsid and NS proteins, can be packaged into infectious particles.

The present invention further provides a compartmentalized kit for the production of a recombinant protein comprising a first container adapted to contain a vector of the present invention wherein said vector comprises the 5' and 3'-termini of AeDNV flanking at least one expression cassette comprising an AeDNV promoter operably linked to a coding region of a heterologous protein or a cloning site. The compartmentalized kit may further comprise additional containers adapted to contain insect host cells, expression vectors encoding NS1 and NS2, insect cells stably expressing NS1 and NS2, or insect cells stably expressing VP1 and VP2.

The invention is further illustrated by the following specific examples which are not intended in any way to limit the scope of the invention.

EXAMPLE 1

Subcloning the AeDNV Genome Into a Plasmid with Multiple Cloning Sites

The AeDNV genome was cloned in pUC19 and designated pUCA. Plasmid pUCA was deposited with the American Type Culture Collection, 12301 Parklawn Drive, Rockville, Md., 20852, on Oct. 19, 1995 and has been accorded ATCC accession Number 97318. DH1 and DH5 strains of *Escherichia coli* were used for cloning procedures as well as for plasmid preparations.

The pUCA plasmid, containing almost the complete genome (3981 nt) of AeDNV, and the plasmid pUCAinv, differing from pUCA only by inversion of the right part of the genome, were constructed from plasmids p19-20, p19-1, and p18-7 (FIG. 1) (Afanasiev et al. 1991, *Virology*, 185:323–336). Plasmid $pUCA_{inv}$ was deposited with the American Type Culture Collection, 12301 Parklawn Drive, Rockville, Md., 20852, on Oct. 19, 1995 and has been accorded ATCC Accession Number 97317. The SacI/EcoRV fragment from p19-20 was transferred into p19-1 to produce the p19-2 plasmid. The plasmid p18-7+ was constructed from p18-7 by insertion of the multiple cloning sites from "pBLUESCRPT" KS phagemid into KpnI/SacI sites. The PstI fragment from p18-7+ was then transferred into p19-2 and, depending on the orientation of the fragment, pUCA and pUCAinv were obtained. The genome of AeDNV in pUCA lacks thirty one nucleotides from the right (5') end of the genome and also some nucleotides from the left (3') extremity (see Afanasiev et al, 1991). However, both ends preserve enough nucleotides to support the secondary structures (hairpins) which are necessary for the excision of a parvovirus genome from a bacterial plasmid and for replication.

The inversion in pUCAinv interrupted the right ORF (coding VPs) and transferred the right-hand palindromic sequences from the extremity into the central part of the genome. This displacement impairs the ability of the virus genome to be excised from the plasmid and replicate.

The plasmids PUCA as well as pUCAinv and all expression constructs based on this clone were very stable even after propagation in DH1 or DH5 strains of *E. coli*. No detectable loss of viral DNA sequences was observed even after large-scale preparation of these clones.

The plasmid pUCANS2 (FIG. 3*f*) was obtained from pUCA after partial digestion with EcoRI and religation. It retains the left half of the AeDNV genome with the mid ORF (for NS2).

EXAMPLE 2

Mosquito Cell Transfection

*Aedes albopictus* cell line C6/36 (ATCC Accession No. CRL-1600) was grown at 28° C. in Leibovitz's L-15 medium (GIBCO) supplemented with 10% fetal bovine serum. Transformation of cells with different plasmids was performed by liposome-mediated transfection using the "LIPOFECTIN" reagent according to the manufacturer's specifications (BRL). Cells were seeded at approximately a 50% monolayer 24 hours prior to transfection. A "LIPOFECTIN"-DNA complex was made by incubating 10 μg (per 25 ml flask) of plasmid DNA with 50 μl of "LIPOFECTIN" reagent in 3 ml of serum-free L-15m medium for 15 min at room temperature. At the same time cells were rinsed three times with sterile PBS (137 mM NaCl, 27 mM KCl, 10 mM $Na_2HPO_4$, 1.8 mM $KH_2PO_4$). The final PBS rinse was removed and replaced with 3 ml of the "Lipofectin"-DNA complex. Following incubation for 8 hours at room temperature, 3 ml of L-15 medium supplemented with 20% fetal bovine serum was added to each flask.

EXAMPLE 3

Testing Infectivity of the AeDNV Genomic Clones

To test the infectivity of the AeDNV genomic clones, pUCA and pUCAinv were transfected into *A. albopictus* C6/36 cells as described in Example 2. As a test for permissiveness, the cells were also infected with purified virus particles. The molar concentration of the virus genomes in the particles added to the cells and in the plasmid samples used for transfection were adjusted to be similar. On the fourth day after infection or transfection (when the cells approached a monolayer), one-tenth of the cells were passed into fresh flasks. The remaining cells were lysed and the low-molecular weight DNA was extracted using a modification of the Hirt procedure (Hirt, B. 1967, *Journal of Molecular Biology* 26:365–369). The Hirt supernatant was extracted twice at room temperature with an equal volume of CHCL3, and the DNA was collected by ethanol precipitation. The precipitated DNA was resuspended in TE buffer, pH 8.0, and digested with pancreatic ribonuclease A (preheated at 80° C. for 10 minutes) at a concentration of 20 μg/ml for 15 minutes at room temperature. After two more extractions with chloroform, DNA was recovered by ethanol precipitation and resuspended in TE buffer. Then half of each sample was digested with DpnI, which in contrast to DpnII cuts only sites that are fully methylated (GmeATC). The DpnI sites of bacterially produced plasmid DNA are fully methylated and can be cleaved by DpnI. The sites in DNA replicated in eukaryotic cells are not methylated and thus not digested by DpnI. Therefore, DpnI can be used to differentiate between input plasmid and DNA that has replicated in eukaryotic cells (Peden et al., 1980, *Science* 209:1392–1396).

After electrophoresis through a 1.2% agarose gel, the DNA was transferred onto a MagnaGraph Nylon (MS1) membrane by standard Southern blot protocol (Southern 1975). Filters were blot dried and baked at 80° C. A Genius nonradioactive DNA labeling and detection kit (Boehringer Mannheim) was used to generate a probe for hybridization to DNA on filters. Blots were prehybridized for two hours in 1× UniBlock (AGTC), 0.1% N-lauroyl sarcosine, 0.02% sodium dodecyl sulfate at 68° C. The prehybridization buffer was replaced with a buffer containing 100 ng of a denatured digoxigenin-labeled DNA probe (synthesized on pUCA) and hybridization was carried out at the same temperature overnight. Synthesis of the probe and immunological detection of DNA after hybridization followed the manufacturer's protocols (Genius kit, Boehringer Mannheim).

Southern blot analysis of the low-molecular weight DNA accumulated in transfected cells after the initial infection and in serial passages (FIG. 2, lanes 1–3) revealed a prominent band of about 4 kb. This is the expected size of the double-stranded monomer replicative form (RF) DNA commonly found in parvovirus-infected cells. A roughly constant amount of the RF monomer was found even in the fourth passage of the cells after infection (FIG. 2, lane 3), demonstrating that this cell line was permissive for AeDNV and that the infection was persistent.

Figure 2:
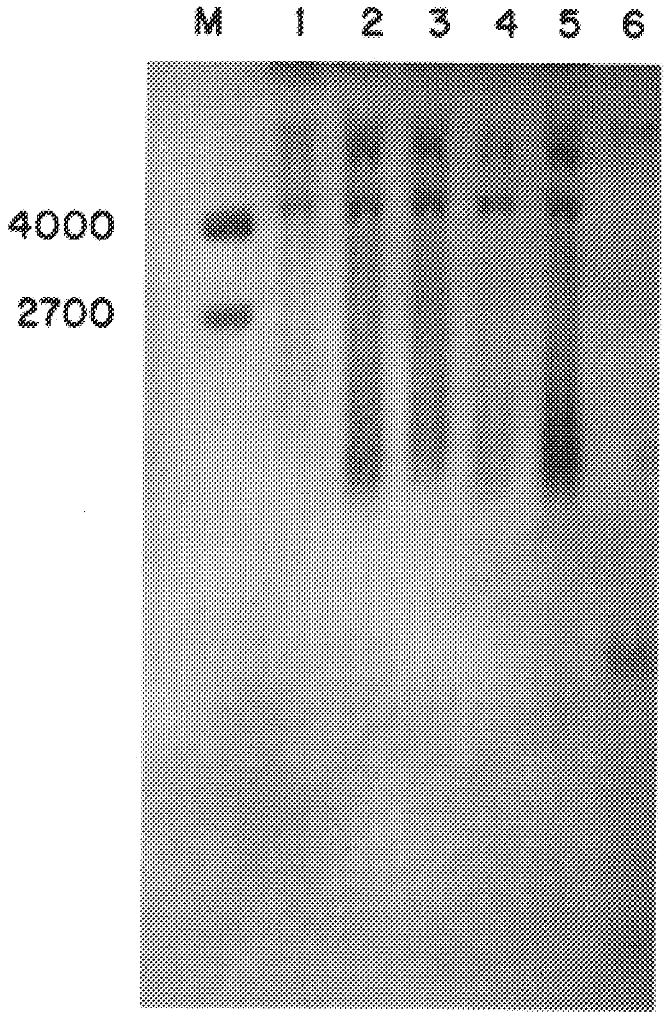
FIG. 2 depicts a Southern blot analysis of intracellular viral DNA induced by transfection of clone C6/36 of *Aedes albopictus* cells with PUCA (lanes 4 and 5) and pUCAinv (lane 6) or by infection with AeDNV particles (lanes 1–3). Lane M shows pUCA cleaved with SacI and XhoI to release the AeDNV genome (upper band, about 4000 nt) and pUC19 plasmid (lower band, about 2700 nt). Lanes 1 to 3, second to fourth serial passages of AeDNV after infection; lanes 4 and 5, initial transfection and first passage of pUCA, respectively; lane 6, initial transfection with pUCAinv (control).

Surprisingly, no cytopathic effect was noticed in the infected C6/36 cells. Cells transfected with the pUCA plasmid yielded a similar 4-kb band (FIG. 2, lanes 4 and 5), but the band was not detected in the cells transfected with the pUCAinv plasmid (FIG. 2, lane 6). The DNA samples shown in FIG. 2 were all digested with DpnI, which cuts only DNA methylated at dam methylation sites. The fact that the DNA from cells transfected with pUCA was resistant to digestion indicates that the DNA must have replicated in mosquito cells where the bacterial methylation pattern was removed. These data indicate that the AeDNV genome was excised from the pUCA plasmid, replicated, and produced an RF monomer of the same size and the same restriction fragment pattern as the wild-type virus. Quantities of the RF monomer accumulated in the cells after transfection with the plasmid and after infection with the virus were similar, reflecting efficient transfection of pUCA into the cells. Thus, pUCA is a fully functional, infectious clone.

EXAMPLE 4

Construction of AeDNV Expression Plasmids

The organization of the AeDNV genome deduced from the published sequence of the AeDNV genome (Afanasiev et al, 1991) is shown in FIG. 3*a*. Based upon the consensus eukaryotic promoter sequences and locations of the large ORF in the AeDNV genome, functional promoters were predicted at map units 0.5, 7, and 61 (taking the length of the AeDNV genome as 100 map units) just upstream of the left ORF, the mid ORF, and the right ORF, respectively. In order to test whether these promoters were functional and could be used for expression of foreign genes, the lacZ gene of *E. coli* encoding β-galactosidase (β-gal) was inserted as a reporter gene into all three plus-strand ORFs as well as into the ORF observed in the negative strand (min ORF).

For constructing AeDNV expression plasmids (FIG. 3), the lacZ gene of *E. coli* was obtained from pMC1871 (Pharmacia). In pMC1871, the N-terminus of the lacZ gene contains multiple cloning sites facilitating insertion of the gene into an open reading frame downstream of host ATG codons. In the following constructs the lacZ gene was inserted into four large open reading frames observed in the AeDNV genome:

pUCAP0.5

The lacZ gene was excised from pMC1871 with SmaI and PstI and ligated into pUCA cleaved with EcoNI, blunt ended with Mung bean nuclease, and then cut with NsiI. In pUCAP0.5, the chimeric β-gal is expressed from the left ORF and contains 47 amino acids of the putative AeDNV NS1. FIG. 3*b*.

pUCAP7

The lacZ gene was excised from pMC1871 with SmaI and PstI and ligated into MscI and NsiI sites of pUCA to express the β-gal gene from the mid ORF. The chimeric product contains 22 amino acids from the N-terminus of the putative AeDNV NS2. FIG. 3*c*.

pUCAP61

The lacZ gene was excised from pMC1871 with SmaI and PstI and ligated in SnaBI and NsiI sites of pUCA, and then, to eliminate NS1 and NS2 coding sequences, the plasmid was cleaved with MscI and religated. In pUCAP61, the chimeric β-gal gene is expressed from the right ORF and contains 38 amino acids from the N-terminus of the putative AeDNV VP1. FIG. 3*d*.

pUCAPmin

Figure 3E:

The lacZ gene was excised from pMC1871 with BamHI, blunt ended with Mung bean nuclease, and ligated into pUCA cleaved with MscI. In pUCAPmin the β-gal gene could be expressed from the min ORF obtaining from the latter only the ATG codon. FIG. 3*e*.

pUCAP0.5-5', pUCAP7-5' and pUCAP61-5'

These plasmids were derived from pUCAP0.5, pUCAP7, and pUCAP61, respectively, by deletion of the right-hand (5') terminus in the AeDNV genome after HindIII cleavage and religation.

The recombinant genes of the above-described expression constructs were designed to produce proteins containing the aminotermini of the corresponding viral proteins fused to the enzymatically active portion of β-gal. The expression plasmids pUCAP0.5, pUCAP7, pUCAP61, and pUCAPmin were introduced into *A. albopictus* C6/36 cells by liposome-mediated transfection as described in Example 2.

EXAMPLE 5

Detection of β-Galactosidase Activity in Transfected Cells

β-galactosidase activity of *A. albopictus* C6/36 cells transfected with the expression plasmids described in Example 4 was detected both by histochemical staining of cells using X-gal as chromogenic substrate and by assaying cell lysates for ability to cleave ONPG.

For histological studies, cells were washed twice with PBS, fixed for five minutes in 0.2% glutaraldehyde, 2% formaldehyde in PBS, washed again, and stained with X-gal solution (1 mg/ml X-gal, 4 mM $K_3Fe(CN)_6$, 4 mM $K_4Fe(CN)_6$, 2 mM $MgCl_2$ in PBS) at 37° C. in the dark. The transfected cells were visualized using an inverted light microscope (Olympus IMT-2). The percentage of transfected cells was determined by dividing the number of cells stained by the total number of cells within a microscopic field.

A spectrophotometric quantification of β-gal specific activity was measured by ONPG (ortho nitrophenyl β-D-galactopyranoside) cleavage assay (Miller 1972 *Experiments in Molecular Genetics*, 432:352–355, Cold Spring Harbor Laboratory Press, Cold Spring Harbor, N.Y.). At 4–5 days post transfection, cells were rinsed two times with PBS, scraped from plates, pelleted five minutes at 750 g, and resuspended in 100 ml of distilled water. After three freeze-thaw cycles (−70° C. to 37° C.), the extract was clarified by centrifugation at 1400 g for ten minutes and divided into two aliquots for protein and ONPG assay. For the ONPG assay, 50 μl of extract, 350 μl Z buffer (60 mM $Na_2HPO_4.7H_2O$0.40 mM $NaH_2PO_4.H_2$, 10 mM KCl, 1 mM $MgSO_4$, 50 mM β-mercaptoethanol-added on day of use) and 80 μl of ONPG (from 4 mg/ml in 0.1M PBS) were incubated at 30° C. until a faint yellow color appeared. The reaction was stopped by the addition of 200 μl of 1M $NaCO_3$, pH 11. Absorbance readings were taken at 420 nm. Total protein concentration was determined spectrophotometrically at 595 nm using Coomassie protein assay reagent (Pierce). Activity was determined according to the following formula:

$$A_{420}\times 380/t(min)/\text{protein}(mg)=\text{units}.$$

Figure 4A:
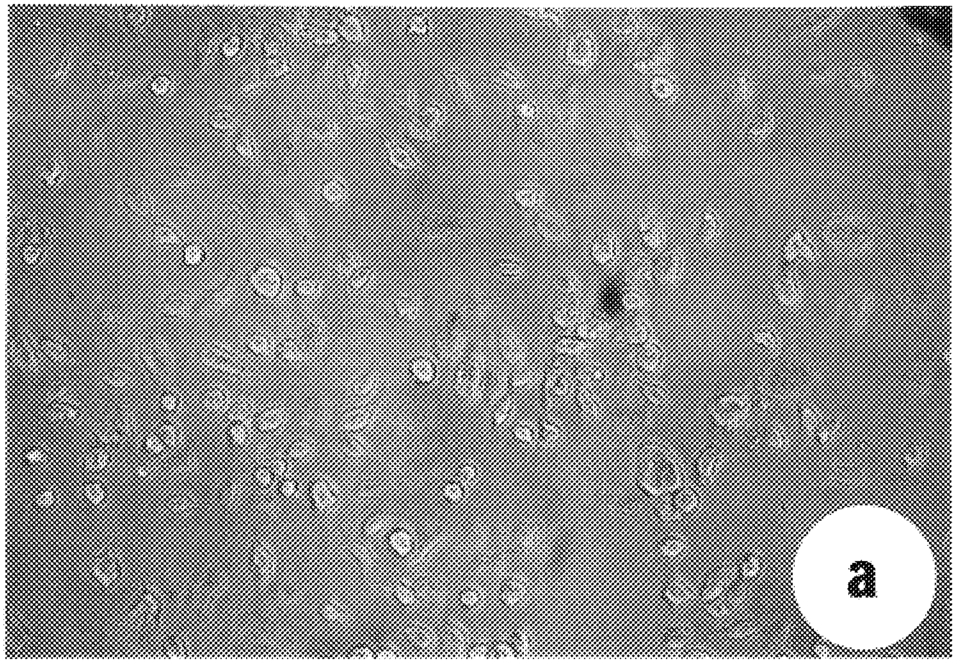
FIG. 4*a* is a photomicrograph (100× magnification) of *Aedes albopictus* C6/36 cells transfected with pUCA and stained with X-gal.
Figure 4B:
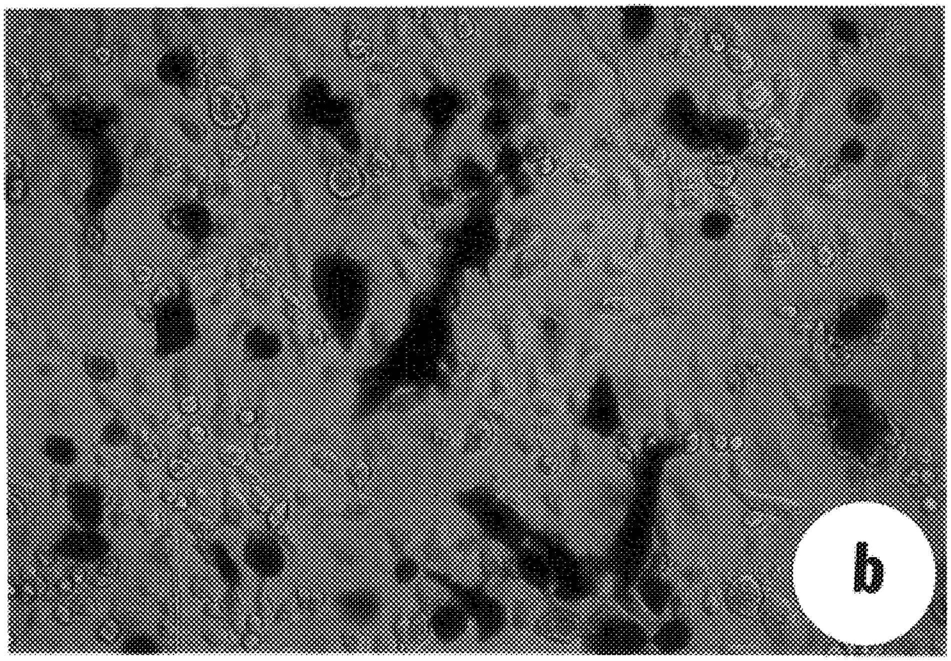
FIG. 4*b* is a photomicrograph (100× magnification) of *Aedes albopictus* C6/36 cells transfected with pUCAP61 and stained with X-gal.

In cells transfected with the pUCAP61 expression plasmid, β-gal activity was detected within 24 hours after transfection, but the maximum number of stained cells (up to 40%) was attained after two days and maintained for at least six days (FIG. 4*b*).

Figure 4C:
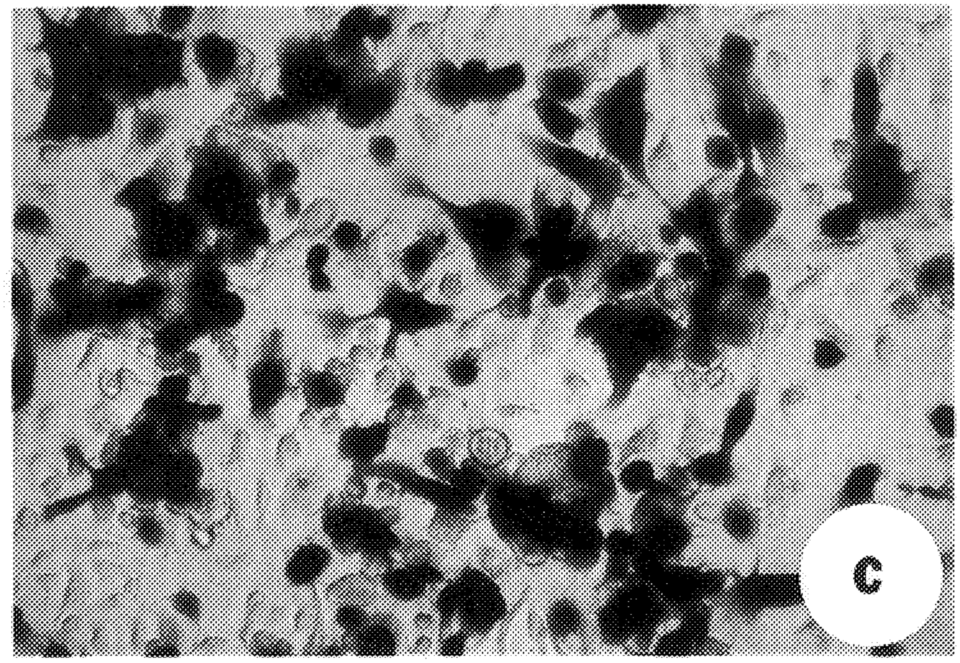
FIG. 4*c* is a photomicrograph (100× magnification) of C6/36 cells transfected with p61 and the helper plasmid pUCAinv expressing NS1 and NS2 stained with X-gal.
Figure 4D:
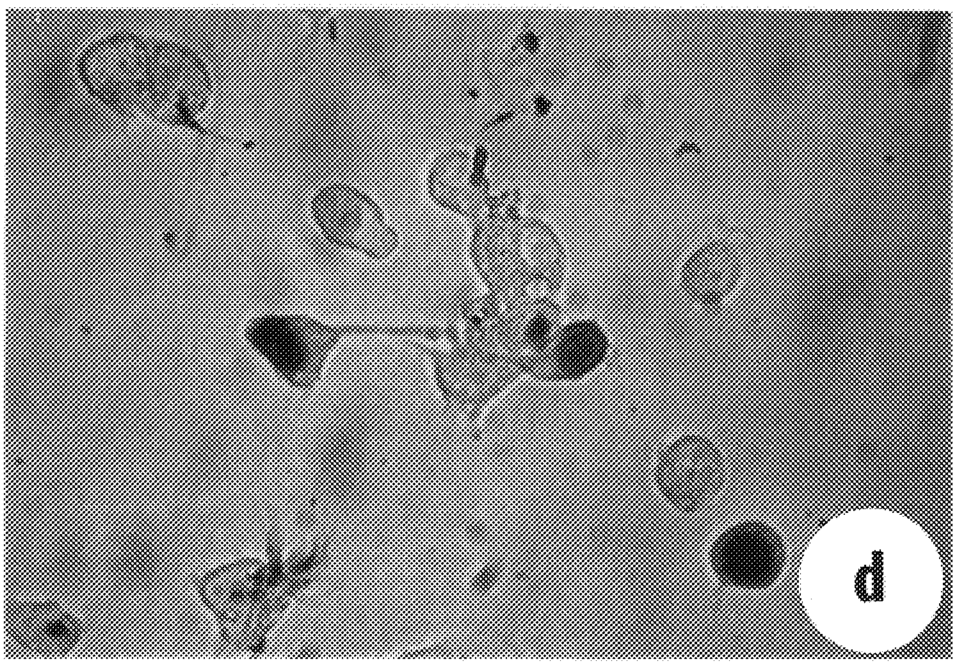
FIG. 4*d* shows nuclear localization of β-gal in C6/36 cells transfected with pUCAP61 (200× magnification).
Figure 4E:
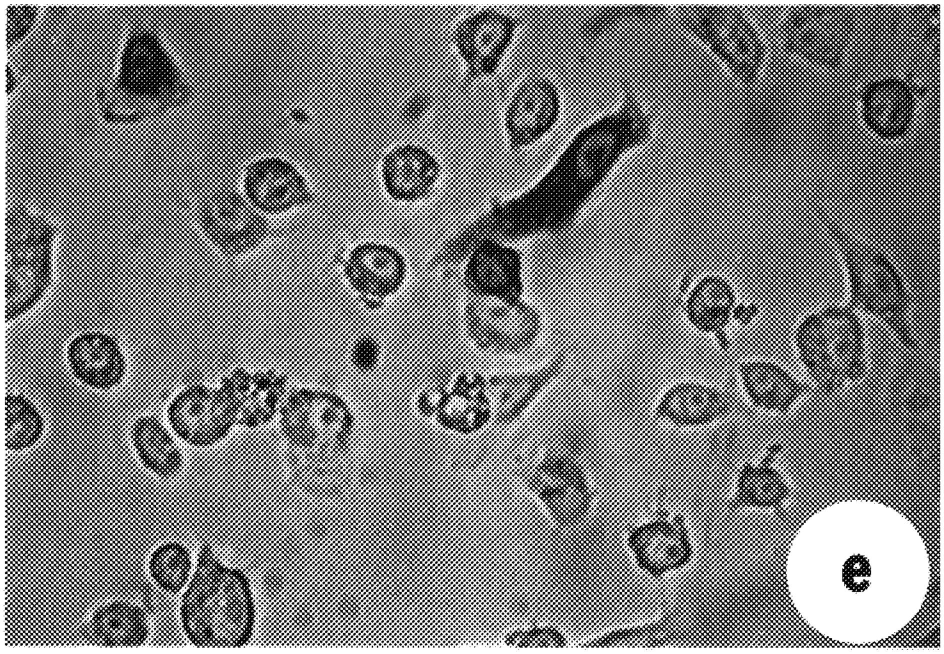
FIG. 4*e* shows cytoplasmic localization of C6/36 cells transfected with pUCAP7 (200× magnification).

Similar results were found for the pUCAP7 plasmid. No staining was detected in control cells transfected with pUCA (FIG. 4*a*). No expression was detected by either histochemical staining or ONPG assay from the pUCAP0.5 or the pUCAPmin plasmids. In cells transfected with pUCAP61 (β-gal gene fused into the right ORF) and stained with X-gal, blue color localized much more intensively in the nucleus than in the cytoplasm (FIG. 4*d*). However, in the case of pUCAP7 (β-gal fused into the mid ORF), staining was predominantly in the cytoplasm (FIG. 4, section E). No preference was found for the β-gal expressed from p0.5. These results show that the AeDNV p7 and p61 promoters are functional promoters. In addition, the chimeric β-galactosidase and likely other heterologous proteins can be targeted to different cellular compartments by the aminoterminal portion of the AeDNV proteins.

EXAMPLE 6

Regulation of Expression from AeDNV Promoters

Figure 5:
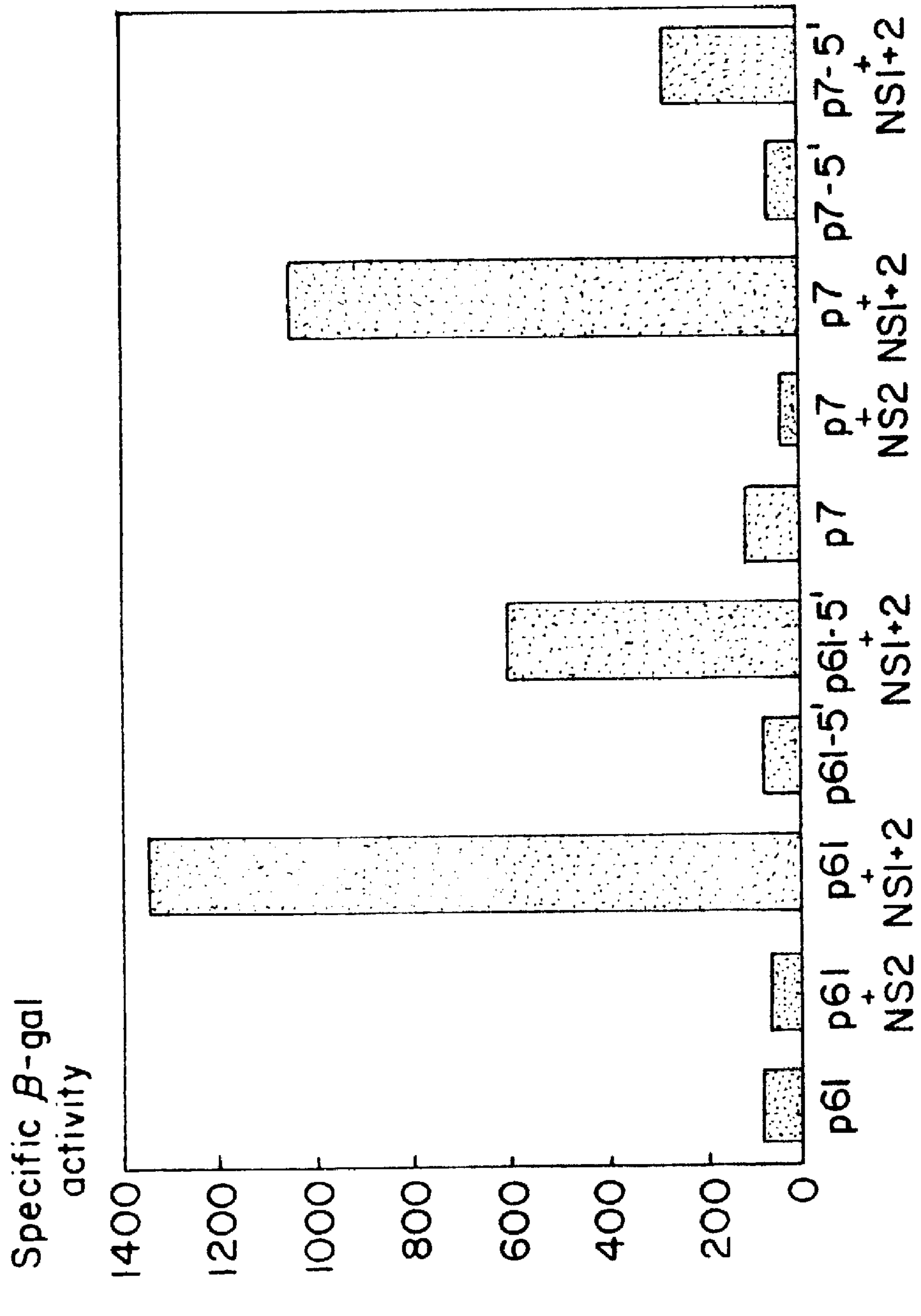
FIG. 5 is a bar graph depicting analysis of β-galactosidase activity in *Aedes albopictus* C6/36 cells transfected (or cotransfected) with different plasmids. NS2 was supplied by the helper plasmid pUCANS2. NS1+NS2 was supplied by the helper plasmid pUCAinv. Activity of the enzyme is expressed as nanomoles of ONPG cleaved/min/mg protein. Data is from a representative experiment.

In order to determine whether expression from the p0.5, p7 and p61 promoters can be regulated by the AeDNV nonstructural proteins (NS1 and NS2), the β-gal expression constructs were cotransfected into C6/36 cells with the helper plasmid pUCAinv, which can express viral proteins from the left ORF (NS1), the mid ORF (NS2), and the minus ORF but not from the right ORF (VPs). The activity of β-gal produced from all three plus-stranded promoters (p0.5, p7, and p61) was stimulated by pUCAinv. The ONPG assay showed that the expression of β-gal from p61 was stimulated about 15-fold in cells transfected with pUCA61 and pUCA-inv (FIG. 5). Approximately 70% of the cells were stained blue with X-gal (FIG. 4*c*). Similar results were obtained with P7 (FIG. 5). A low level of expression was detected from pUCAP0.5 (less than 1% of cells in a flask were stained blue). No expression was detected from pUCAPmin.

Figure 3F:
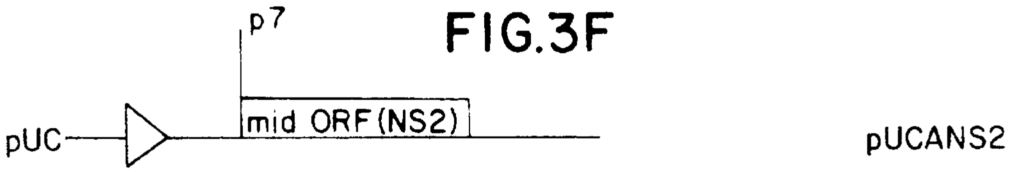

In order to determine whether NS2 alone could stimulate expression, the plasmids were cotransfected into the cells with pUCANS2, a plasmid bearing the gene for NS2 only (FIG. 3*f*). No increase in the expression was detected from any of the promoters (FIG. 5). Thus, NS2 alone is not sufficient for the stimulation of β-gal expression.

The stimulation of β-gal activity, observed after cotransfection of the expression constructs with the helper plasmid pUCAinv could be explained by trans-activation of the corresponding promoters by the non-structural proteins (NS1 alone or with the proteins expressed from the mid ORF and minus ORF) or by the excision and replication of the recombinant virus genome resulting in an increased copy number of the LacZ gene. To determine the molecular mechanisms involved, expression plasmids were constructed (for all three promoters) in which the right end of the AeDNV DNA containing the inverted repeats was deleted, (see Example 4) thereby rendering the recombinant genomes incapable of excision and replication even in the presence of the AeDNV NSs. These constructs were cotransfected with the helper plasmid pUCAinv into C6/36 cells. An increase in the β-gal activity was detected, but the level of the stimulation was reduced 2 to 3 fold (for p7 and p61, see FIG. 5). Thus, the stimulation of expression results from both trans-activation of the promoters and excision and replication of the recombinant virus genomes.

These results indicate that trans-activation of the p0.5, p7 and p61 promoters in heterologous expression vectors can be achieved by cotransfection of a helper plasmid comprising coding sequence for NS1 and NS2.

EXAMPLE 7

Generation of Transducing Particles

In the previous examples, the expression constructs were delivered into the cells by liposome-mediated transfection. In this example, the heterologous gene was packaged into AeDNV particles and delivered to other cells by the infectious process.

First, cells were cotransfected with different β-gal expression plasmids and the pUCA clone, which supplies both nonstructural and capsid proteins. Fresh cultures of C6/36 cells were infected with cell-free lysates obtained on the fourth day after such contransfections. Three days after infection, the cells were analyzed for β-gal activity by X-gal staining. Different numbers of blue cells were detected depending on the size of the recombinant expression construct used in the experiment and on the ratio of the helper plasmid cotransfected. In the control experiment in which the expression constructs were not cotransfected with the helper plasmid, no cells were stained. In the most successful experiment (pUCAP7 cotransfected with pUCA with the molar ratio of 1:2), the β-gal activity was detected in almost 20% of cells.

Figure 6:
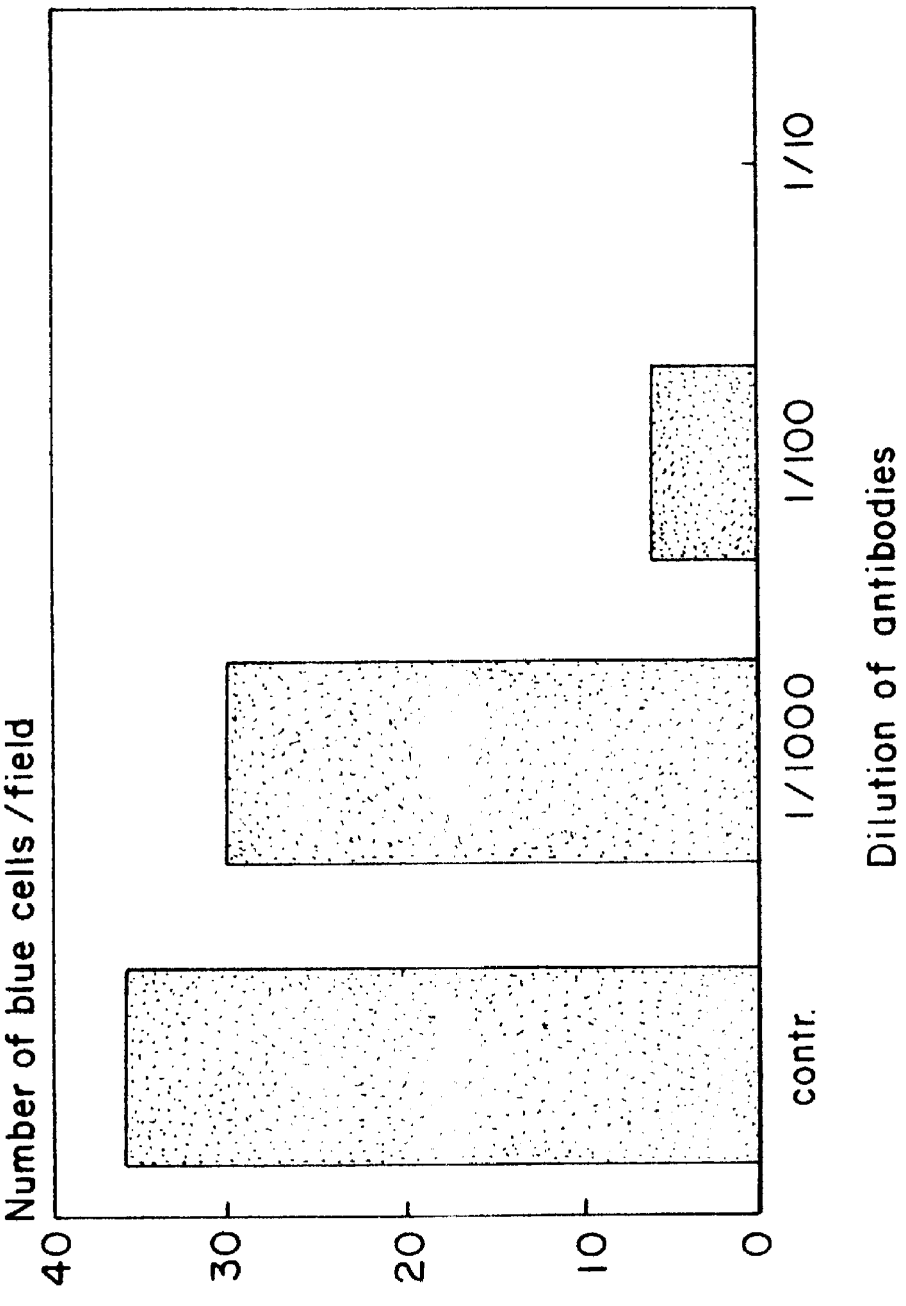
FIG. 6 is a bar graph depicting inhibition of transduction of β-gal activity by antibodies prepared against the AeDNV particles. Data is from a representative example.

In order to confirm that this β-gal activity had been transduced by infectious virions only, the cell-free lysate was incubated for one hour at room temperature with rabbit antibodies prepared against the AeDNV particles before layering onto fresh cells. The incubation of the lysate with different amounts of antibodies led to a titratable reduction in the number of blue cells, and at the highest concentration of antibodies, no blue cells were detected at all (FIG. 6). This indicates that the β-gal activity detected in the cells is the result of packaging of the β-gal recombinant genome into AeDNV virions followed by particle-mediated delivery of lacZ gene to the fresh cells, or in other words, transduction.

The efficiency of transduction was a function of the length of the recombinant genome. Recombinant genome pUCAP61 (8% longer than the wild type) was packaged less efficiently than pUCAP7 (2% longer). No transduction was detected for the construct that was 60% longer (the same as pUCAP61 but without the internal deletion; see FIG. 3).

EXAMPLE 8

Recombinant Protein Production by Transduction

A transformed *A. albopictus* C6/36 cell line which is resistant to hygromycin and constitutively expresses the structural proteins VP1 and VP2 of AeDNV was obtained as follows.

Figure 7:
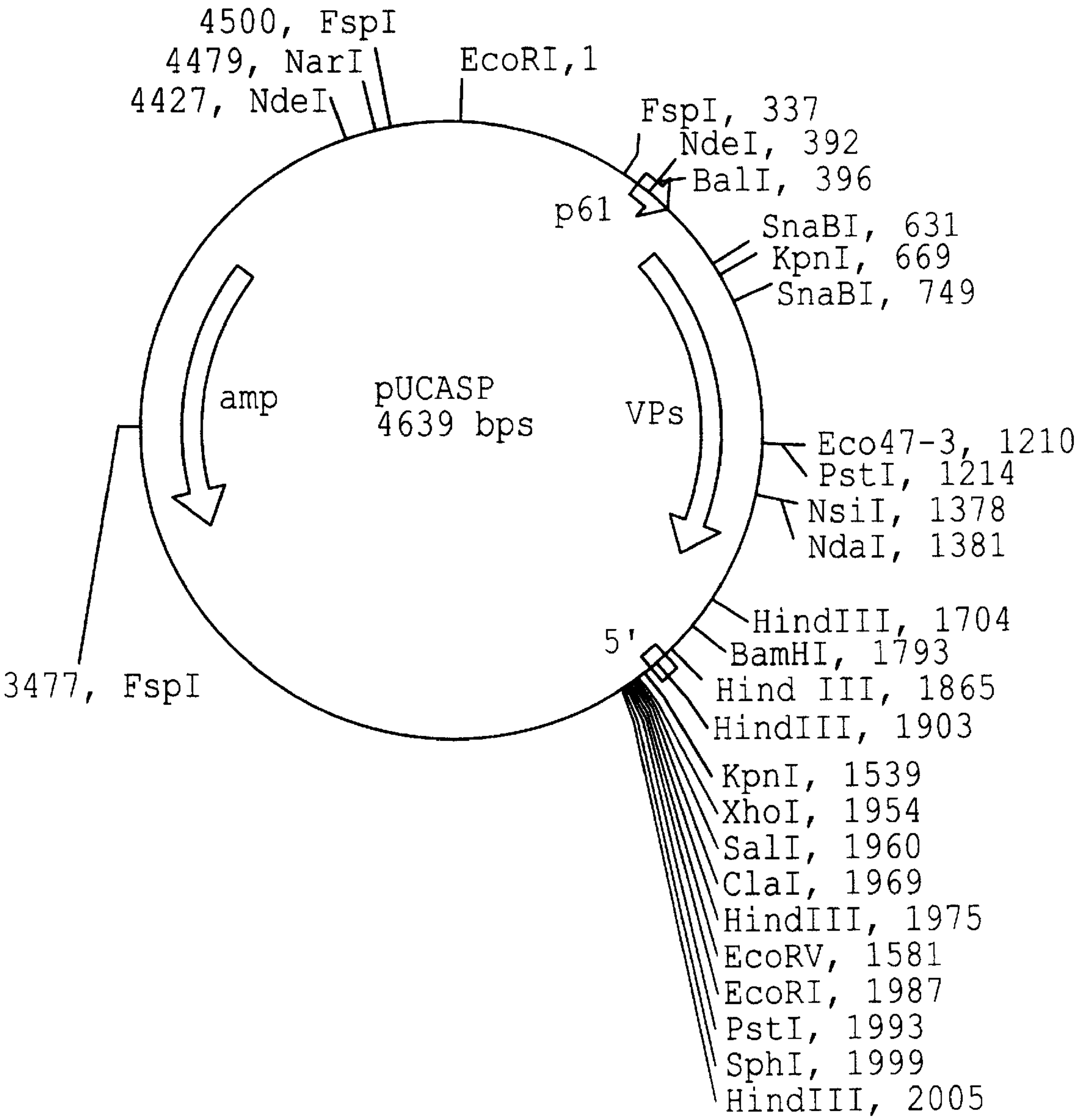
FIG. 7 depicts plasmid pUCASP.

The pUCA plasmid described in Example 1 was digested with SacI and NcoI, and the larger fragment was isolated, trimmed with mung bean nuclease and religated. The resulting plasmid, designated pUCASP, contains the p61 promoter and coding regions of VP1 and VP2 proteins of AeDNV (FIG. 7).

Figure 8:
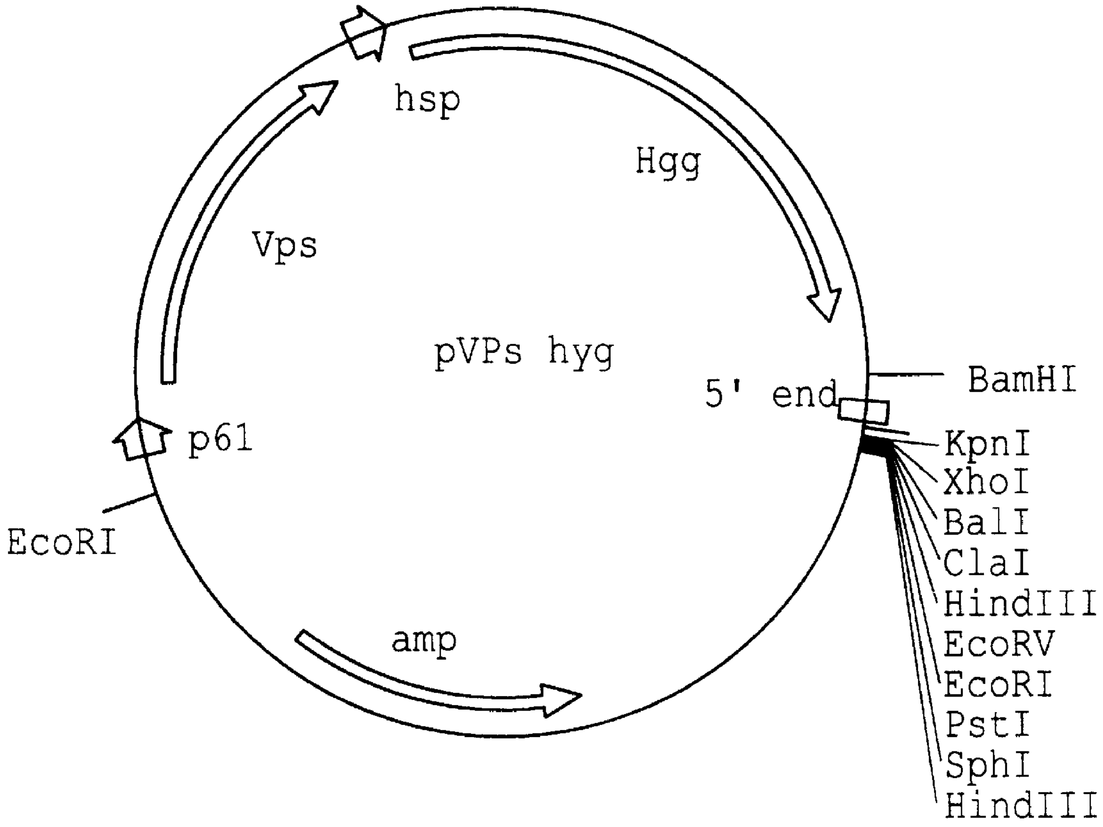
FIG. 8 depicts plasmid pVPsHyg.

The pUCASP plasmid was digested with BamH1 and ligated with a BamH1 fragment carrying the hygromycin phosphotransferase gene under the control of the heat shock 70 promoter (hsp). The resulting plasmid, designated pVPsHyg, can express both the AeDNV structural proteins and the hygromycin phosphotransferase gene (FIG. 8).

The pVPsHyg plasmid was transfected into *A. albopictus* C6/36 cells. Transfected cells were subjected to hygromycin selection. In two weeks six colonies of hygromycin resistant cells were observed in culture flasks. These colonies were transferred into separate flasks and maintained.

The presence of the AeDNV structural proteins was confirmed using rabbit antibodies raised against the AeDNV virus particles. Antibodies bound to cells expressing AeDNV VPs were detected using antirabbit goat antibodies coupled with fluoresceinisothiocyanate. Three cell colonies showed the presence of the AeDNV proteins with one (No. 3) exhibiting especially bright staining in more than 50% of the cells, implying a very efficient level of AeDNV VP expression.

The ability of the transformed C6/36 cells to produce recombinant proteins was confirmed as follows.

Figure 9:
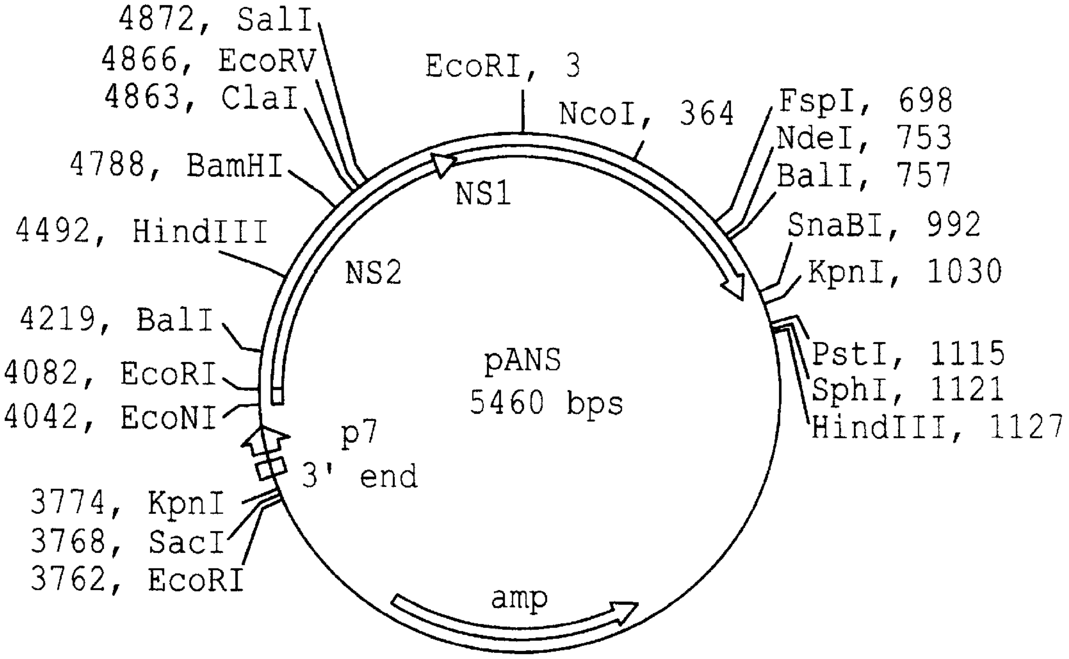
FIG. 9 depicts plasmid pANS.

The No. 3 cells were co-transfected with the expression plasmid pUCAp7 containing the lacZ reporter gene (FIG. 3*c*) and the plasmid pANS (FIG. 9). The plasmid pANS is a derivative of pUCA in which only the nonstructural proteins of AeDNV are retained. Four days after transfection, cell free lysate was layered onto fresh C6/36 cells.

Four days after infection the cells were stained with Xgal solution. A number of cells were stained blue. In a control experiment in which cells were initially transfected with only pUCAP7 no stained cells were detected. This experiment demonstrates that the β-gal activity was transferred to the fresh cells by the transducing particles, and that the transformed cells are a good supplier of the AeDNV structural proteins.

5' and 3'-termini of AeDNV genomic DNA flanking at least one expression cassette comprising an AeDNV promoter and a cloning site wherein said cloning site is positioned relative to said promoter such that a heterologous gene inserted into said cloning site is operably linked to said promoter; and a second container containing an expression vector comprising the coding region of AeDNV VP1 and VP2 operably linked to a promoter.

What is claimed is:

1. A method of producing a recombinant protein comprising: transfecting an insect cell that stably expresses Aedes Densonucleosis Virus (AeDNV) VP1 and VP2 with an expression vector comprising the 5' and 3'-termini of AeDNV genomic DNA flanking at least one expression cassette comprising an AeDNV promoter operably linked to the coding sequence of said protein and an expression vector comprising the AeDNV NS1 and NS2 genes; obtaining infectious virions from said transfected cell; infecting a second insect cell with said infectious virions; culturing said second cell under conditions whereby said protein is expressed; and recovering said recombinant protein from said second insect cell.

2. The method of claim 1 wherein said AeDNV promoter is p0.5, p7 or p61.

3. The method of claim 1 wherein said insect cell is a mosquito cell.

4. The method of claim 3 wherein said mosquito cell is an *A. aegypti* or *A. albopictus* cell.

5. A compartmentalized kit for the production of a recombinant protein comprising a first container containing at least one of an expression vector comprising the 5' and 3'-termini of AeDNV genomic DNA flanking at least one expression cassette comprising an AeDNV promoter operably linked to a heterologous gene or an expression vector comprising the 5' and 3'-termini of AeDNV genomic DNA flanking at least one expression cassette comprising an AeDNV promoter and a cloning site wherein said cloning site is positioned relative to said promoter such that a heterologous gene inserted into said cloning site is operably linked to said promoter; and a second container containing an expression vector comprising the coding region of AeDNV VP1 and VP2 operably linked to a promoter.

6. The compartmentalized kit of claim 5 further comprising a third container containing insect cells stably expressing AeDNV NS1 and NS2.

7. The compartmentalized kit of claim 5 further comprising a third container containing insect host cells.

8. The compartmentalized kit of claim 7 wherein said insect host cells are *A. aegypti* or *A. albopictus* cells.

9. The compartmentalized kit of claim 5 further comprising a third container containing an expression vector comprising the p0.5 promoter and left ORF of AeDNV.

10. The compartmentalized kit of claim 9 further comprising a fourth container containing insect host cells.

11. The compartmentalized kit of claim 10 wherein said insect host cells are *A. aegypti* or *A. albopictus* cells.

12. A compartmentalized kit for the production of a recombinant protein comprising at least one of an expression vector comprising the 5' and 3'-termini of AeDNV genomic DNA flanking at least one expression cassette comprising an AeDNV promoter operably linked to a heterologous gene or an expression vector comprising the 5' and 3'-termini of AeDNV genomic DNA flanking at least one expression cassette comprising an AeDNV promoter and a cloning site wherein said cloning site is positioned relative to said promoter such that a heterologous gene inserted into said cloning site is operably linked to said promoter, and a second container containing insect cells stably expressing AeDNV VP1 and VP2.

* * * * *

UNITED STATES PATENT AND TRADEMARK OFFICE

CERTIFICATE OF CORRECTION

PATENT NO. : 5,849,523

DATED : December 15, 1998

INVENTOR(S) : B.N. Afansiev, et al.

It is certified that error appears in the above-identified patent and that said Letters Patent are hereby corrected as shown below:

On The Title Page, [56] References Cited, PUBLICATIONS: "differen" should read --different--

Column 13, Line 13: "pBLUESCRPT" should read --pBLUESCRIPT--

Signed and Sealed this

First Day of May, 2001

*Attest:*

NICHOLAS P. GODICI

*Attesting Officer*

*Acting Director of the United States Patent and Trademark Office*